United States Patent [19]

Baran

[11] 4,226,642
[45] Oct. 7, 1980

[54] SYSTEM PROVIDING FOR DECONTAMINATION WASHING AND/OR BIOCIDAL TREATMENT

[75] Inventor: Walter J. Baran, Erie, Pa.

[73] Assignee: American Sterilizer Company, Erie, Pa.

[21] Appl. No.: 9,815

[22] Filed: Feb. 6, 1979

[51] Int. Cl.³ .............................................. B08B 3/10
[52] U.S. Cl. ...................................... 134/10; 134/18; 134/30; 134/36; 134/37; 134/56 R; 134/95; 134/102; 366/165; 422/295
[58] Field of Search .................... 134/10, 18, 25 A, 29, 134/30, 36, 37, 56 R, 57 R, 95, 102; 422/26, 106, 295, 297; 366/107, 165, 3, 10

[56] References Cited

U.S. PATENT DOCUMENTS

| 654,647 | 7/1900 | Koppelmann | 134/30 X |
| 2,289,890 | 7/1942 | Walter | 134/25 A X |
| 3,007,478 | 11/1961 | Leonhardt et al. | 134/95 X |
| 3,034,520 | 5/1962 | Jewell | 134/99 |
| 3,088,180 | 5/1963 | Lauterbach | 422/26 X |
| 3,586,294 | 6/1971 | Strong | 366/165 |

FOREIGN PATENT DOCUMENTS 947699 1/1964 United Kingdom ...................... 422/20

OTHER PUBLICATIONS

"Medallion" Series, SC-341, Pamphlet by Amsco Automatic Washer-Sterilizer, Oct. 1975.
Journal of Hospital Research, Research and Educational Divisions of the American Sterilizer Company, vol. 2, No. 2, Jul. 1964.

Primary Examiner—Richard V. Fisher
Attorney, Agent, or Firm—Shanley, O'Neil and Baker

[57] ABSTRACT

Methods and apparatus providing for decontamination washing and/or biocidal treatment of articles, including washing and sterilizing of surgical instruments in a single chamber, are disclosed. Air is delivered under pressure for injection at the bottom of the chamber through a plurality of inlets positioned to provide interaction of their horizontally oriented discharges including formation of turbulent vortices. Upward movement of air creates vertically oriented cleaning turbulence. Spray means are provided to remove loose soil before washing and to remove soil separated by washing. Drainage removal of soil from the chamber is verified by a drain probe. Steam sterilization at pressures above atmospheric provides for sterilization at temperatures of 250° F. and higher.

20 Claims, 5 Drawing Figures

SYSTEM PROVIDING FOR DECONTAMINATION WASHING AND/OR BIOCIDAL TREATMENT

This invention is concerned with methods and apparatus for decontamination washing and/or biocidal treatment of articles including washing and sterilizing of surgical instruments in a single chamber operable at pressures other than atmospheric. More particularly, the invention is concerned with removing soil from such articles brought about by forced injection of air forming coacting discharges providing effective soil removal throughout the chamber.

The complexity of surgical instrument design and nature of surgical soil are obstacles to proper cleaing of surgical instruments for reuse. Multiple joints, hinges, crevices or serrated edges make access to soil difficult and the soil itself, usually protein or other organic material, is often hardened in place by drying. Also, soiled instruments should be disinfected with a minimum of handling to reduce risk to personnel.

Commercially available washer-sterilizers provide a washing phase in which loose soil is removed by overflow of a washing liquid at one side of the chamber while steam and air are injected into the washing liquid from opposite sides of the chamber. After the washing phase, the washing liquid is forced from the chamber by steam which initiates a sterilization phase.

Significantly improved cleaning effectiveness and cleaning efficiency are brought about with the present invention by better preparation of the goods for washing and a washing system which creates unique vortex-like turbulence and other movements throughout the chamber to provide improved decontamination of surgical instruments enabling direct sterilization and reuse of the surgical instruments without intermediate handling.

Other advantages and contributions of the invention are set forth in describing a specific embodiment of the invention as shown in the accompanying drawings. In these drawings.

Figure 1:
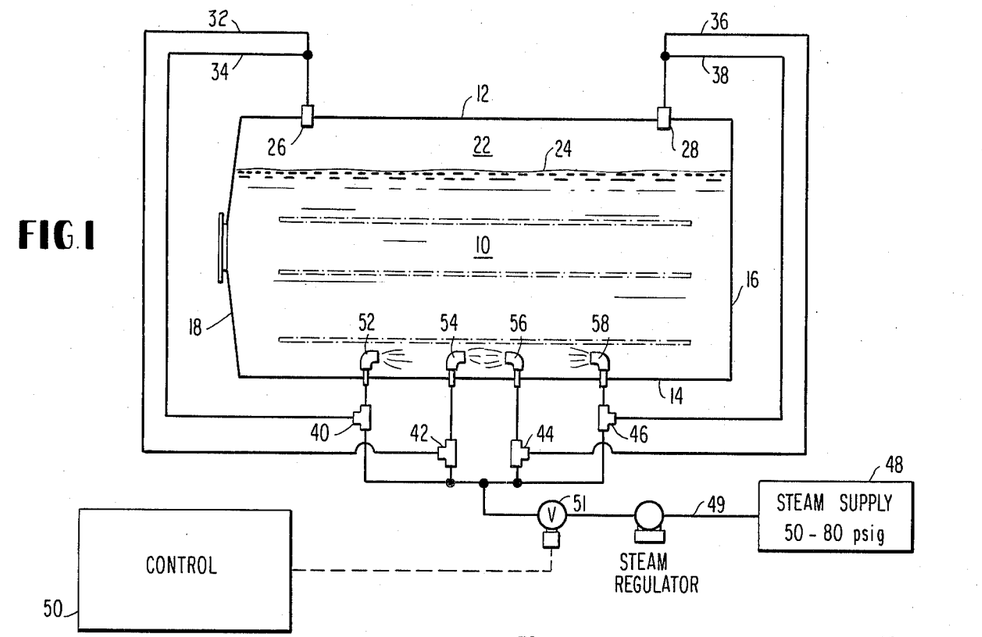
FIG. 1 is a schematic illustration of washing and biocidal treatment apparatus of the invention in the washing phase.
Figure 2:
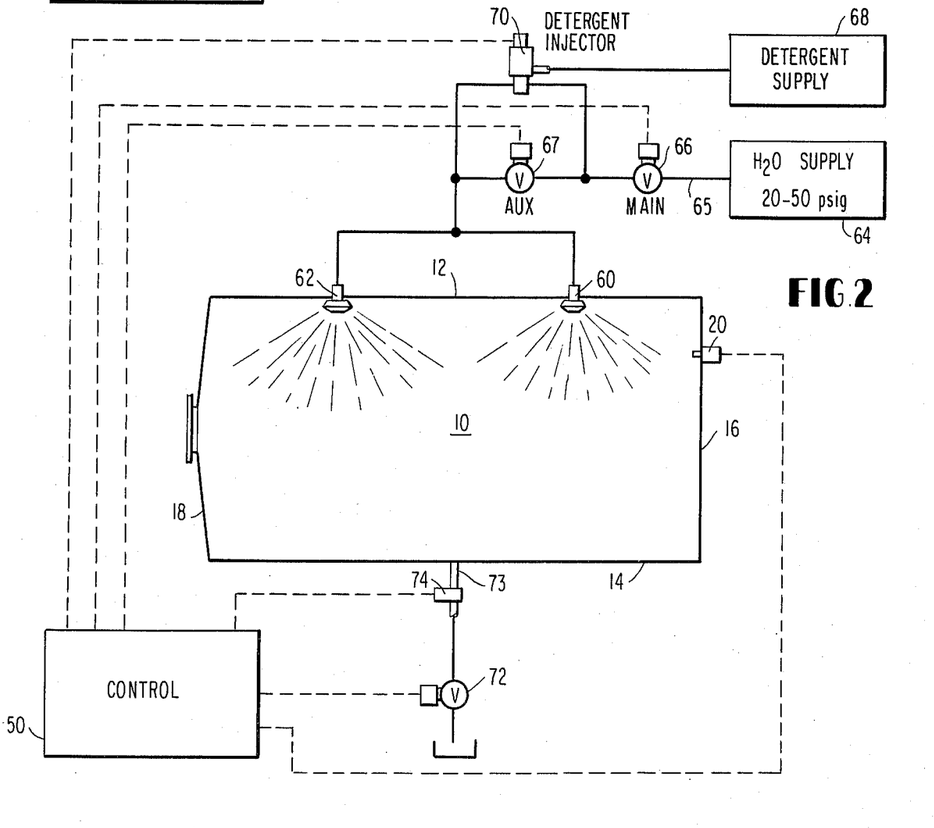
FIG. 2 is a schematic illustration of washing and biocidal treatment apparatus of the invention in a spray phase.
Figure 3:
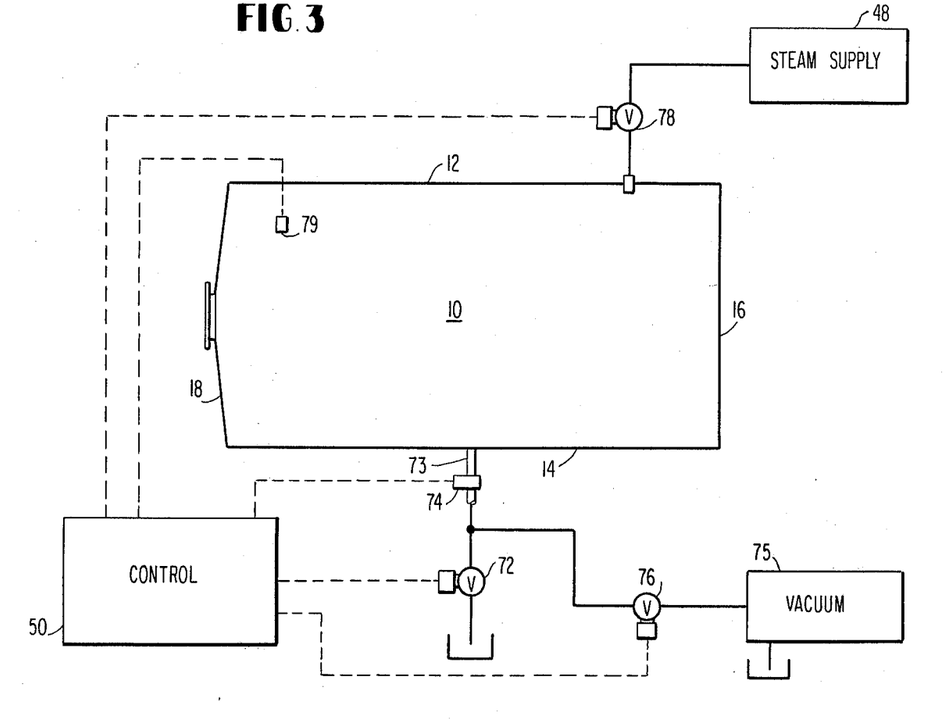
FIG. 3 is a schematic illustration of washer-sterilizer apparatus of the invention in the sterilizing phase.

While phases of the novel washer-sterilizer cycle are depicted separately in FIGS. 1, 2 and 3 for purposes of description, preparation, washing, and sterilizing phases of the invention are carried out in the same chamber to which the separately depicted elements are connected.

Chamber 10 is defined by a shell which includes a top wall 12, bottom wall 14, back wall 16, and closure door 18. Control of inlet and outlet conduits to chamber 10 and sealing of door 18 permit operation of chamber 10 at pressures other than atmospheric. The chamber shell can be a conventional pressure vessel as used in conventional steam sterilizers adapted with fittings for liquid addition and removal; a shell with dimensions of approximately 16"×16"×28" is described in the specific embodiment.

After loading of the chamber and pre-wash preparation of the articles to be cleaned and sterilized, the washing liquid level (FIG. 1) in chamber 10 is established by water level probe 20 (FIG. 2). A predetermined air-space volume 22 above washing liquid level 24 provides a source of air for a closed loop air system.

Because of the uniformity of the novel cleaning action turbulence throughout the washing liquid volume provided by the invention, support racks (shown in dotted lines in FIG. 1) for surgical instrument trays can be placed throughout the washing liquid volume including the lower portion of the chamber where obstacles to proper cleaning were pronounced in commercially available washer-sterilizers.

After establishing washing liquid level, air is injected into the washing liquid by a unique arrangement of inlets with interacting discharges. In the embodiment shown, air is withdrawn from air space 22 at locations 26, 28. Conduits 32, 34, 36, and 38 form part of a continuous loop and provide for delivery of air to air-steam mixers 40, 42, 44, and 46. Steam from source 48 is delivered through conduit 49. Control 50 actuates solenoid valve 51 to deliver steam to the air-steam mixers 40, 42, 44, and 46 which comprise venturi-action ejectors; the air-steam mixers withdraw air from air space 22 and propel an air-steam mixture for injection subsurface of washing liquid level 24 and, vertically below the load, through air-steam inlets 52, 54, 56, and 58. The chamber itself then completes the continuous loop to the air withdrawal ports 26, 28.

In preparation for washing, loose soil is removed from the goods to be cleaned by pre-wash spraying through nozzles 60, 62 (FIG. 2). Water, under pressure from source 64, is directed along conduit 65 which includes solenoid operated main water valve 66 and auxiliary water valve 67. Injection of a chemical additive, e.g. a wetting agent or detergent, with the pre-wash spray liquid is optional. Introduction of a chemical additive into the washing liquid is carried out in a predetermined manner by control 50 through additive injector 70.

The pre-wash spray liquid, which can be preheated, from nozzles 60, 62 removes loose soil particles from the goods. Drain valve 72 in drain line 73 is maintained open by control 50 to remove such soil from the chamber. The duration of pre-wash rinse is preselected. In a representative cycle with a surgical instrument load, a pre-wash can be carried out in about two minutes. Water level probe 74 in drain line 73 verifies that the pre-wash spray liquid and the soil it is carrying are being removed from the system.

Upon completion of the load preparation spraying, and verification that the chamber 10 and drain line 73 are empty by drain line sensor means 74, the drain valve 72 is closed. The valves in conduit 65 to water supply 64 are opened. After initiation of water supply to the chamber, auxiliary valve 67 is closed so that detergent from supply 68 can be automatically and proportionally added through additive injection means 70.

Washing liquid fill continues to a level controlled by probe 20. Air space volume is increased over that provided in conventional washer-sterilizers because of the amount of air used. The air-steam ratio is significantly higher than in commercially available washer-sterilizers. In accordance with the invention, the air-steam ratio should be about 2:1, by weight, and greater. Providing a greater air space or other measures can be taken in order to avoid substantial carry-over of water droplets in the air stream.

The air plays a significant role in supplying and delivering energy and movement for the unique turbulent action created in the vortex configuration turbulence induced in the washing liquid. Air injection in accordance with the invention provides a violent scrubbing action. In the embodiment shown, air and steam under pressure are injected through injector inlets 52, 54, 56, 58 positioned in the chamber bottom wall to provide unique turbulent vortices moving horizontally about the chamber.

Figure 4:
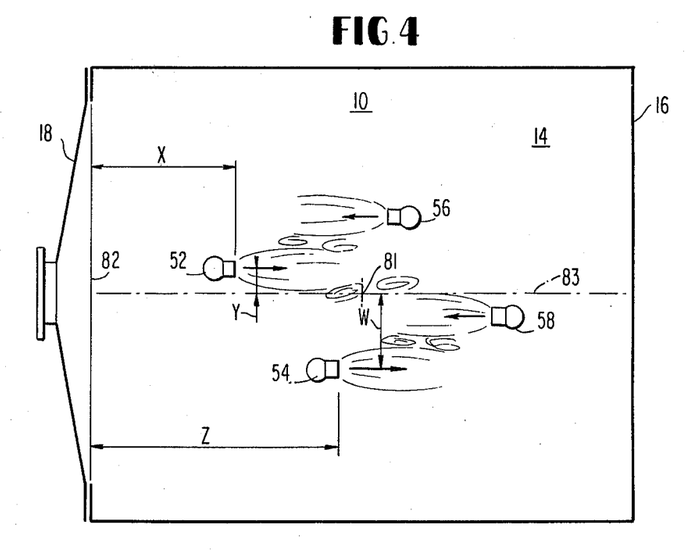
FIG. 4 is a plan view showing positioning of air injection means to provide interaction of air discharges.

The air-steam injector inlets 52, 54, 56 and 58 are arranged in juxtaposition as shown in FIG. 4 about midpoint 81 of the horizontal cross section of the chamber. With the positioning shown, no special nozzle configuration is required. The air-steam inlet openings are oriented with a major component of discharge in the horizontal plane. Also, each of the outlets is oriented with a major component of discharge oriented inwardly, i.e. toward the midpoint 81.

A coaction results because of the relative positioning and direction of the discharges of inlets 52 and 56 which are substantially opposite in direction. Similarly, the discharges of outlets 54 and 58 are substantially opposite. The horizontally oriented discharges pass in contiguous relationship. Washing liquid at the periphery of the discharge plumes is accelerated in opposite directions and interacts. Numerous washing liquid vortices of turbulence are formed between each pair of oppositely directed discharges. Similar vortex-like turbulence is created by the discharge relationship from outlets 52 and 58. These vortices of washing liquid turbulence, tornado-like in action and configuration, are generated rapidly and move horizontally about the chamber. Such individual vortices of turbulence move about the lower portion of the chamber providing a cleaning action about such lower portion of the chamber which was not previously available. Also, the upward movement of air from the air-steam inlets provides an upward movement for the turbulent vortices and the water above each inlet. A vertical shearing-like action is created in the washing liquid areas above each injector discharge. The upward movement of air from the individual outlets presents a cyclic relative movement vertically between columns of washing liquid above each inlet discharge. The water level rises and follows above each inlet creating a kinetic wave-like action moving across the upper surface which indicates that the vertical shearing action extends throughout the washing liquid volume so that load support rack means can be positioned throughout such volume.

Placement of the air-steam injectors in the bottom portion of the chamber vertically below the load to obtain this multi-directional turbulence is shown in the plan view of FIG. 4. The horizontal cross section midpoint of bottom wall 14 is located at point 81. The juxtaposition of the injection openings about midpoint 81 provides coaction between their discharges generating turbulent vortices and upward movement which maximizes turbulence, scrubbing action, and cleaning effectiveness and efficiency.

Preferably, an equal number of air-steam injectors are positioned longitudinally and laterally of the horizontal plane in symmetrical relationship about midpoint 81. In the embodiment of FIG. 4, with a bottom wall with dimensions of approximately 16"×26", four injectors are used. Cylindrical conduit openings, without special nozzle contouring, are adequate for injection; the inlets are oriented for horizontal discharge. The discharge of injector inlet 52 is directed longitudinally toward midpoint 81 and front closure rim 82; inlet 52 is substantially half-way between the closure rim 82 and the midpoint 81. In the lateral dimension, inlet 52 is positioned a short distance from longitudinal axis 83, about one-eighth the distance from the longitudinal centerline 83 toward the side wall. Dimension "X" in the 16"×26" bottom can be about 7" and dimension "Y" about ½".

In relation to inlet 52, injector conduit inlet 54 is spaced a greater distance from and on the opposite side of longitudinal centerline 83; outlet 54 is also positioned a greater distance from front rim 82 than outlet 52, i.e. closer to the midpoint 81. In the longitudinal dimension, the inlet 54 is spaced about 5/6ths of the distance from the front rim 82 to the centerpoint 81. In a 16"×26" bottom wall, dimension "Z" is about twelve inches and dimension "W" between two and three inches.

Both inlets 52 and 54 face midpoint 81 and the rear wall 20. The injector inlet 56 is positioned substantially symmetrically, in relation to the horizontal plane midpoint 81, as inlet 54. The injector inlet 58 is positioned substantially symmetrically, with relation to the midpoint 81 as the injector inlet 52. The direction of discharge from each is shown. The circular configurations represent the turbulent vortices being generated by the interaction of the discharges of each pair of inlets.

Such washing liquid turbulence is established throughout the washing liquid volume covering the load support rack space in the chamber for perforated surgical instrument trays. The washing liquid performs the scrubbing action with the air bubbles providing the driving energy and generally upward movement. An interaction between the turbulent vortices and upward movement provides a scrubbing action in all directions about the load providing access to joints, hinges, crevices, and the like.

The continuous loop conduits 32, 34, 36, and 38 can include steam traps. Also, other venting arrangements can be used to limit pressure build-up during the wash phase in the confined air space of a sterilizing chamber to facilitate upward movement of air in the sterilizing chamber. Air injection is continued for a predetermined period to complete removal of soil from the articles being washed. Air under pressure from other sources than the chamber can be provided and injected.

Referring to FIG. 2, upon the completion of the wash phase, drain valve 72 is opened. Typically, wash liquid is removed by gravity. Drainage of the wash liquid is verified by drain line probe 74.

The drain is maintained open and a rinse liquid is sprayed from nozzles 60, 62 over the goods to remove any soil which may have been suspended in the washing liquid and redeposited on the goods during drainage. Spray rinsing, with the drain open to remove any soil from the chamber, continues for a predetermined period to assure removal of soil from the goods and the chamber.

Upon completion of the spray rinsing and verification of drainage, a conditioning phase for load sterilization is initiated. Valve 78 is opened to inject steam from source 48 (FIG. 3) into the chamber. With the drain valve 72 open, steam flows through the chamber 10 removing air which, because of its insulating properties, would delay heating of the load. Fast exhaust can be provided, e.g. by exposure of the chamber to vacuum source 75 by opening valve 76. Steam flow through the chamber is continued for the time required to substantially completely eliminate air from the chamber. Then, drain valve 72 is closed and steam is continued to be added to the chamber to raise chamber pressure to establish the desired temperature. Steam sterilization is carried out at above 250° F. and higher.

Steam pressure and sterilizing times are dependent on the temperature and degree of sterilization desired; steam pressure is sensed by pressure sensing means 79. When sterilizing with steam at approximately 270° F., the steam pressure and steam temperature are maintained for approximately three minutes. Upon completion of the sterilization phase, drain valve 72 is opened. Return of chamber pressure level to atmospheric completes the cycle; fast exhaust may be provided by vacuum source 75.

With the teachings of the invention and the unique washing action provided, a decontamination washing can be selected or washing and biocidal treatment, including terminal sterilization, can be selected.

The chamber, conduit connections to the chamber, valving arrangements on such conduits, steam ejectors, water spray nozzles, detergent injector, chamber pressure sensor, and water level probes are readily available commercially and require no further description for an understanding of the invention. Also, in the light of the above disclosures, those skilled in the art can use electromechanical or electronic elements, which are known and commercially available, when combined as taught above and shown in the control schematic of FIG. 5 to carry out the sequence of steps in the pre-wash preparation, washing, and sterilizing phases of the present washer-sterilizer cycle.

Figure 5:
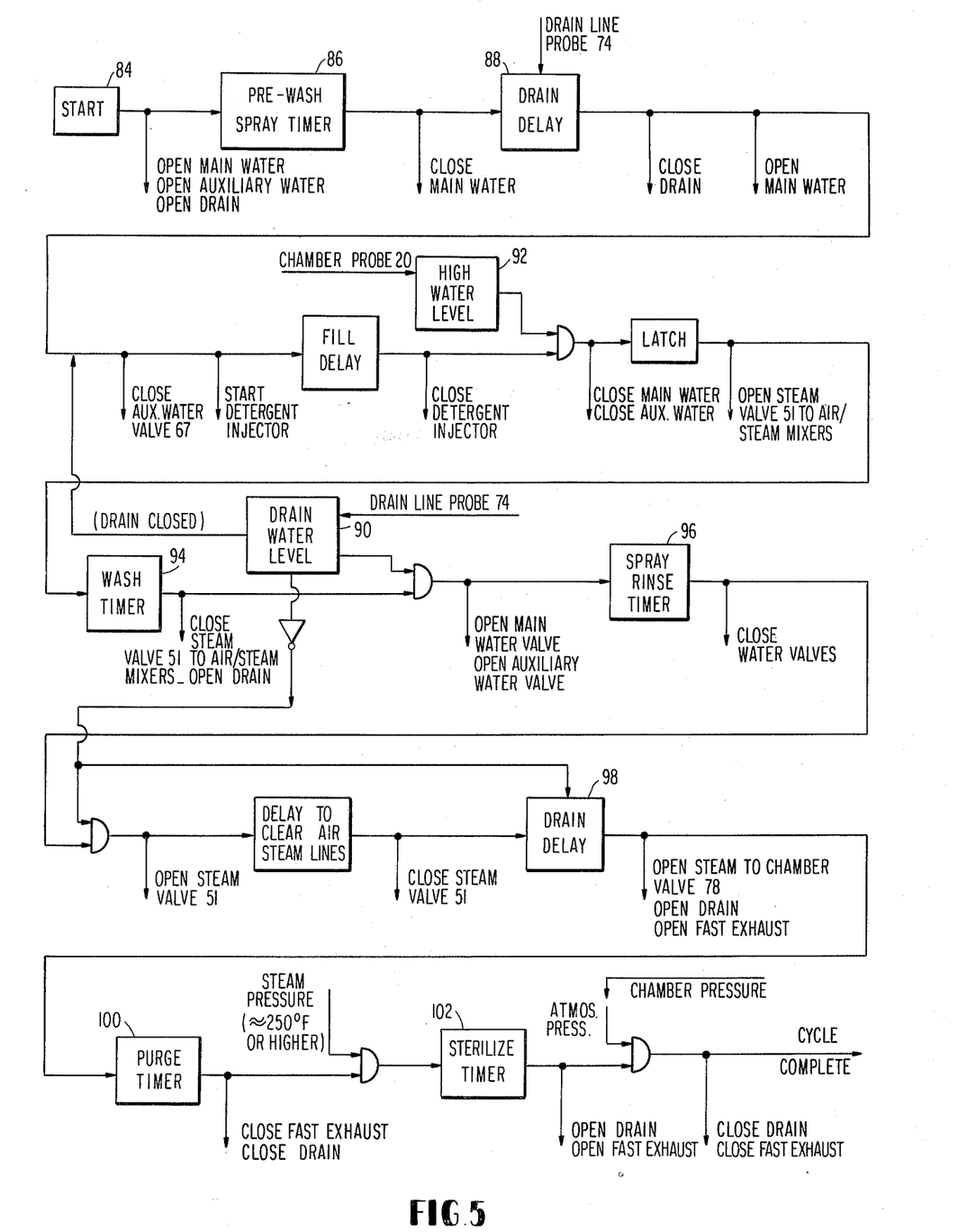
FIG. 5 is a control schematic for carrying out the invention.

Referring to FIG. 5, after loading the chamber 10 and closing door 18, the cycle is initiated at start switch 84 which opens water supply valves including main and auxiliary valves 66, 67 to source 48, and opens chamber drain 72. Pre-wash preparation spraying is carried out for a predetermined period by pre-wash spray timer 86. The main water valve 66 is then closed and sequencing is delayed at drain delay means 88 for verification of drainage after which, the drain is closed.

The main water valve 66 is then opened with start of water fill verified by drain line probe 74 through drain water level signal means 90. Then, the auxiliary water valve 67 can be closed and proportional addition of detergent initiated at injector 70. After completing detergent injection, washing liquid addition is terminated by a signal from chamber water level probe 20 through high water level signal means 92. When injecting air with steam, the steam valve 51 is then opened to the steam ejector air-steam mixers and the washing cycle is carried out for a predetermined period by wash timer 94. After completion of the wash cycle, steam valve 51 is closed and the drain opened.

When chamber drainage is verified through drain level signal means 90, the water valves are opened to spray nozzles 60, 62. The spray rinse valves are maintained open under the control of spray rinse timer 96.

Upon completion of the spray rinse, the water valves are closed. Steam valve 51 is again opened to clear the lines, between the steam ejector air-steam mixers and the chamber, of water. Steam valve 51 is then closed. Drainage is verified by low level probe 74 with sequencing delayed as required by drain delay means 98. Sequencing then continues with a signal from the low chamber level signal means 90.

With the drain valve open, chamber steam valve 78 is opened and air is removed by gravity as steam is injected through the upper wall portion of the chamber; fast chamber exhaust, by vacuum means 80, can be utilized. Removal of air by the steam continues under the control of purge timer 100.

After chamber purge, the drain valve is closed, and the fast exhaust, if utilized, is terminated. Steam at the required pressure to provide a desired sterilizing temperature, generally above about 250° F., is added to the chamber and the chamber is held at the desired elevated sterilizing temperature for a preselected period by sterilizing timer 102.

Upon completion of the sterilizing treatment, the drain is opened and fast exhaust initiated to return the chamber to atmospheric pressure. Upon verification that atmospheric pressure is established in the chamber, through pressure sensor 79, the drain and fast exhaust are closed, the cycle is complete, and the door 18 released for opening.

Representative dimensions and values for carrying out the improved washing or washing-sterilizing cycles have been set forth for a chamber with dimensions of approximately 16"×16"×28". With these teachings, values for differing chamber sizes and other modifications can be made by those skilled in the art while utilizing the principles of the invention. Therefore, in evaluating the scope of the present invention, reference should be made to the appended claims.

I claim:

1. Method in which articles are cleaned of soil and biocidally treated in a single chamber capable of operating at pressures other than atmospheric comprising the steps, after articles forming a load to be washed and biocidally treated are placed in the chamber and closing of an access door, of controllably filling the chamber with washing liquid to a selected level covering the load while establishing a confined air space volume in an upper portion of the chamber above such washing liquid level, injecting air under pressure subsurface of the washing liquid level through a plurality of inlets having discharges spaced vertically below the load at a bottom portion of the chamber including at least a pair of inlets positioned in relation to each other to provide an interaction of their discharges on the washing liquid, such discharges having a major component of discharge oriented horizontally in the bottom portion of the chamber and further oriented with a major component of discharge in the direction of the remaining inlet of the pair such that air discharges from the pair of inlets while exhibiting a major horizontal component pass in contiguous relationship propelling washing liquid in opposite directional relationship forming vertically oriented turbulent vortices in the washing liquid by contiguous passage of such discharges, such vertically-oriented turbulent vortices moving horizontally about the chamber into contact with the load, such air injection further causing upward movement of air and washing liquid in the chamber, interrupting such air injection, and biocidally treating such washed articles in the chamber to provide a desired sterilization level.

2. The method of claim 1 in which such injection of air is carried out through a plurality of pairs of inlets with interacting discharges perdeterminedly distributed horizontally of the chamber in symmetrical relationship about a midpoint of a horizontal cross section of the chamber, such plurality of inlets being located at substantially the same horizontal level in the bottom portion of the chamber.

3. The method of claim 1 including the steps of removing loose soil from the load and the chamber in preparation for such washing by spraying a rinse liquid onto the goods from a location vertically spaced above the load, draining the chamber of such spray liquid, sensing drainage of such spray liquid from the chamber before adding washing liquid and, after washing and interrupting air injection, draining the chamber of the washing liquid, then spray rinsing the goods with a rinsing liquid to remove soil from the load which might have been redeposited during drainage of the washing liquid, and sensing drainage of such rinse liquid from the chamber before biocidally treating the articles.

4. The method of claim 1 in which such biocidal treatment comprises steam sterilization including the steps of injecting steam into the upper portion of the chamber to flow by gravity over the load for discharge from the bottom portion of the chamber, then sealing the chamber for operation above atmospheric pressure, adding steam under pressure to establish a temperature within the chamber at a temperature above about 250° F., and maintaining such temperature in the chamber for a predetermined time interval.

5. Method in which articles are cleaned of soil and biocidally treated in a single chamber capable of operating at pressures other than atmospheric comprising the steps, after articles forming a load to be washed and biocidally treated are placed in the chamber and closing of an access door, of controllably filling the chamber with washing liquid to a selected level covering the load while establishing a confined air space volume in an upper portion of the chamber above such washing liquid level, withdrawing air from the confined air space volume in the chamber by steam ejector means, combining the withdrawn air and steam for injection into the chamber, injecting such air and steam under pressure subsurface of the washing liquid level and spaced vertically below the load through a plurality of inlets at a bottom portion of the chamber including at least a pair of inlets positioned in relation to each other to provide an interaction of their discharges on the washing liquid, such discharges having a major component of discharge oriented horizontally in the bottom portion of the chamber and further oriented with a major component of discharge in the direction of the remaining inlet of the pair such that turbulent vortices are formed in the washing liquid by contiguous passage of such discharges, interrupting such air and steam injection, and biocidally treating such washed articles in the chamber to provide a desired sterilization level.

6. The method of claim 5 including controlling the ratio of air to steam in the air-steam combination within a predetermined range in which weight of air exceeds the weight of steam.

7. Method in which articles are cleaned of soil and biocidally treated in a single chamber capable of operating at pressures other than atmospheric comprising the steps, after articles forming a load to be washed and biocidally treated are placed in the chamber and closing of an access door, of controllably filling the chamber with washing liquid to a selected level covering the load while establishing a confined air space volume in an upper portion of the chamber above such washing liquid level, providing a plurality of inlets at a bottom portion of the chamber including at least a pair of inlets positioned in relation to each other to provide an interaction of their discharges on the washing liquid, providing continuous-loop interconnection for passage of air from the confined air space in the upper portion of the chamber above the washing liquid level, supplying steam within a desired pressure range above atmospheric pressure, withdrawing air from such confined air space volume above the washing liquid level in the chamber, combining such air and steam for injection into the washing liquid at the bottom portion of the chamber, injecting such air and steam under pressure subsurface of the washing liquid level for discharge through such plurality of inlets, such discharges from the pair of inlets having a major component of discharge oriented horizontally in the bottom portion of the chamber and further oriented with a major component of discharge in the direction of the remaining inlet of the pair such that turbulent vortices are formed in the washing liquid by contiguous passage of such discharges, interrupting such air and steam injection, and biocidally treating such washed articles in the chamber to provide a desired sterilization level.

8. Method for decontamination washing of articles comprising the steps, after articles forming a load to be washed are placed in a chamber, of controllably filling the chamber with washing liquid to a selected level covering the load, injecting air under pressure subsurface of the washing liquid level through a plurality of inlets located at a bottom portion of the chamber having discharges spaced vertically below the load, discharging such air through at least a pair of such plurality of inlets positioned in relation to each other to provide an interaction of their discharges on the washing liquid, such discharges being directed to have a major component of discharge horizontally of the bottom portion of the chamber and further oriented with a major component of such discharge being in the direction of the remaining inlet of the pair such that air discharges from the pair of inlets while exhibiting a major horizontal component pass in contiguous relationship propelling washing liquid in opposite directional relationship forming vertically oriented turbulent vortices in the washing liquid between such discharges, such vertically-oriented turbulent vortices moving horizontally about the chamber into contact with the load, such air injection further causing upward movement of air and washing liquid in the chamber, continuing such air injection for a predetermined time period, then interrupting such injection, and draining washing liquid from the chamber.

9. The method of claim 8 in which such injection of air is carried out through a plurality of pairs of inlets with interacting discharges, such inlets being predeterminedly distributed at substantially the same horizontal level in the bottom portion of the chamber and in symmetrical relationship to a midpoint of a horizontal cross section of the chamber.

10. The method of claims 8 or 9 further including heating the washing liquid by injecting steam into the washing liquid in the chamber by combining steam with the air injected into the chamber, and controlling the ratio of air to steam in the air-steam combination within a predetermined range in which weight of air exceeds the weight of steam.

11. The method of claim 8 including the steps of removing loose soil from the load and the chamber prior to adding washing liquid by spraying a liquid onto the load from a location vertically spaced above the load in the upper portion of the chamber, draining the chamber of such spray liquid, sensing such drainage of the spray liquid before adding washing liquid and, after washing and interrupting air injection, draining the chamber of the washing liquid, and then spray rinsing the goods with a rinsing liquid to remove soil from the load which might have been redeposited during drainage of the washing liquid.

12. Method for decontamination washing of articles comprising the steps, after articles forming a load to be washed are placed in a chamber, of controllably filling the chamber with washing liquid to a selected level covering the load, providing a plurality of inlets located at a bottom portion of the chamber with discharges subsurface of the washing liquid level and spaced vertically below the load, providing continuous-loop interconnection for passage of air from the chamber above the washing liquid level to such chamber location subsurface of the washing liquid level, supplying steam within a desired pressure range above atmospheric pressure of steam ejector means in such continuous-loop interconnection to withdraw air from the chamber above the washing liquid level, combining such withdrawn air and steam for injection subsurface of the washing liquid in the chamber, discharging such air and steam through at least a pair of such plurality of inlets position in relation to each other to provide an interaction of their discharges on the washing liquid, such discharges being directed to have a major component of discharge horizontally of the bottom portion of the chamber and further oriented with a major component of such discharge being in the direction of the remaining inlet of the pair such that air discharges from the pair of inlets while exhibiting a major horizontal component pass in contiguous relationship propelling washing liquid in opposite directional relationship forming vertically oriented turbulent vortices in the washing liquid between such discharges, such vertically-oriented turbulent vortices moving horizontally about the chamber into contact with the load, such air injection further causing upward movement of air and washing liquid in the chamber, continuing such air injection for a predetermined time period, then interrupting such injection, and draining washing liquid from the chamber.

13. Washing-sterilizing method in which medical articles such as surgical instruments are cleaned of soil and sterilized in a single chamber capable of operating at pressures other than atmospheric comprising the steps, after articles forming a load to be washed and sterilized are placed in the chamber and closing of an access door, of removing loose soil from the load and the chamber in preparation for washing, then controllably filling the chamber with washing liquid to a selected level covering the load while establishing a confined air space volume in the chamber above such washing liquid level, providing continuous-loop interconnection for passage of air from the confined air space in the chamber above the washing liquid level to a chamber location subsurface of the washing liquid level and spaced vertically below the load in a bottom portion of the chamber, supplying steam within a desired pressure range above atmospheric pressure to steam ejector means connected in the continuous-loop interconnection to withdraw air from the air space volume above the washing liquid level in the chamber, combining such withdrawn air and steam for injection of air and steam into the washing liquid level at the bottom of the chamber, injecting such combination of air and steam for a preselected time interval into the chamber from a plurality of horizontally discharging inlets with interaction discharges which form turbulent vortices and upwardly moving turbulence in washing liquid in the chamber, then, after completion of such washing phase, interrupting such air and steam injection, draining the chamber of the washing liquid, then spray rinsing the goods with a rinsing liquid to remove soil from the load which might have been redeposited from the washing liquid, draining rinse liquid from the chamber, flowing steam through the chamber with an open drain to remove air by gravity, then sealing the chamber and adding stem under pressure to raise the temperature of the articles above about 250° F. to provide a desired sterilization, and then reducing chamber pressure to atmospheric to permit opening of the chamber for removal of the washed and sterilized articles.

14. Apparatus for cleaning soil from and biocidally treating articles forming a load in a single chamber capable of operating at pressures other than atmospheric, comprising a sealable chamber defined by wall portions including a closure door, such wall portions defining an upper chamber portion and a bottom chamber portion spaced vertically below the load, means for adding a washing liquid to the chamber, means controlling filling of the chamber with washing liquid to a selected level covering the load and establishing a confined air space volume in the chamber above such washing liquid level, air injection means for injecting air into the chamber subsurface of the washing liquid level at a plurality of locations in such bottom portion of the chamber, such air injection means including at least a pair of inlets oriented to have a major component of discharge in a horizontal plane with each discharge having a major component directed toward the remaining inlet of the pair such that their discharges pass in contiguous relationship with horizontally disposed discharges interacting on washing liquid to form turbulent vortices, means for controlling injection of air for a preselected time interval into the washing liquid in the chamber, drain means for the chamber including controllable valve means, and means for biocidally treating the goods for a preselected time interval to provide a desired sterilization level.

15. The apparatus of claim 14 in which the air injecting means comprises a plurality of pairs of air inlets distributed about the bottom portion of the chamber in symmetrical relationship to a midpoint of the horizontal cross section of the chamber, such air inlets being oriented to have a major component of air discharge direction toward such midpoint of the horizontal cross-sectional plane of the chamber.

16. The apparatus of claim 14 in which the means for biocidally treating the load include steam sterilizing means for injecting and maintaining steam under pressure in the chamber for a predetermined period.

17. Apparatus for cleaning soil from and biocidally treating articles forming a load in a single chamber capable of operating at pressures other than atmospheric, comprising a sealable chamber defined by wall portions including a closure door, such wall portions defining an upper chamber portion and a bottom chamber portion spaced vertically below the load, means for adding a washing liquid to the chamber, means controlling filling of the chamber with washing liquid to a selected level covering the load and establishing a confined air space volume in the chamber above such washing liquid level, continuous-loop interconnection means for passage of air from the confined air space in the chamber above the washing liquid level for injection subsurface of the washing liquid level at the bottom portion of the chamber, injection means for injecting such air into the chamber subsurface of the washing liquid level at a plurality of locations in such bottom portion of the chamber, such air injection means including at least a pair of inlets oriented to have a major component of discharge in a horizontal plane with each discharge having a major component directed toward the remaining inlet of the pair such that their discharges pass in contiguous relationship with horizontally disposed discharges interacting on washing liquid to form turbulent vortices, means for controlling injection of air for a preselected time interval into the washing liquid in the chamber, drain means for the chamber including controllable valve means, and means for biocidally treating the goods for a preselected time interval to provide a desired sterilization level.

18. The apparatus of claim 17 further including means for supplying steam within a desired pressure range above atmospheric pressure, steam ejector means for withdrawing air from the confined air space volume above the washing liquid level in the chamber, and means forming part of the continuous-loop interconnection air passage means for conveying combined air and steam to the chamber.

19. Apparatus for decontaminating articles by turbulent washing comprising a chamber for holding articles to be washed, such chamber including a bottom portion vertically spaced below articles to be washed, means for controllably adding washing liquid to the chamber to fill the chamber to a level covering articles to be decontaminated, means supplying air under pressure for injecting into the washing liquid, injection means for injecting air into the washing liquid comprising a plurality of inlets located in the bottom portion of the chamber including at least a pair of inlets each positioned in relation to each other to discharge air under pressure with a major component directed horizontally of the chamber and directed toward the remaining inlet of the pair such that the discharges from the pair of inlets pass each other in contiguous relationship so as to interact forming turbulent vortices in the washing liquid, and means for draining washing liquid from the chamber.

20. The apparatus of claim 19 in which the means for injecting air under pressure include means for injecting steam for discharge of air and steam under pressure into the washing liquid and in which such plurality of inlets include a plurality of pairs of inlets distributed substantially symmetrically with relation to the midpoint of a horizontal cross section of the chamber at substantially the same horizontal level in the bottom portion of the chamber.

* * * * *

UNITED STATES PATENT AND TRADEMARK OFFICE
CERTIFICATE OF CORRECTION

PATENT NO. : 4,226,642

DATED : October 7, 1980

INVENTOR(S) : Walter J. Baran

It is certified that error appears in the above-identified patent and that said Letters Patent are hereby corrected as shown below:

Column 1, line 14, "cleaing" should be --cleaning--.

Column 7, line 1, "perdeterminedly" should be --predeterminedly--.

Column 9, line 50, "of" should be --to--.

Column 10, line 54, "stem" should be --steam--.

Signed and Sealed this

Twenty-seventh Day of January 1981

[SEAL]

Attest:

Attesting Officer

RENE D. TEGTMEYER

Acting Commissioner of Patents and Trademark